(12) United States Patent
Wang et al.

(10) Patent No.: US 10,203,307 B2
(45) Date of Patent: Feb. 12, 2019

(54) MICROFLUIDIC DEVICES FOR LIQUID CHROMATOGRAPHY-MASS SPECTROMETRY AND MICROSCOPIC IMAGING

(71) Applicant: The Regents of the University of California, Oakland, CA (US)

(72) Inventors: Daojing Wang, Moraga, CA (US); Pan Mao, Fremont, CA (US); Rafael Gomez-Sjoberg, Menlo Park, CA (US); Hung-Ta Wang, Tuscaloosa, AL (US); Peidong Yang, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 262 days.

(21) Appl. No.: 14/729,999

(22) Filed: Jun. 3, 2015

(65) Prior Publication Data
US 2015/0293063 A1 Oct. 15, 2015

Related U.S. Application Data

(63) Continuation of application No. PCT/US2013/073022, filed on Dec. 4, 2013.
(Continued)

(51) Int. Cl.
*G01N 30/06* (2006.01)
*H01J 49/04* (2006.01)
(Continued)

(52) U.S. Cl.
CPC ........ *G01N 30/06* (2013.01); *B01L 3/502753* (2013.01); *G01N 30/6095* (2013.01);
(Continued)

(58) Field of Classification Search
CPC ............ H01J 49/0431; G01N 30/6095; B01L 2300/0861
See application file for complete search history.

(56) References Cited

U.S. PATENT DOCUMENTS 5,500,071 A * 3/1996 Kaltenbach ....... B01L 3/502707
156/257
5,571,410 A * 11/1996 Swedberg ......... B01L 3/502707
204/451

(Continued)

OTHER PUBLICATIONS

International Search Report and Written Opinion for International Application No. PCT/US2013/073022 dated Dec. 2, 2013.
(Continued)

*Primary Examiner* — Harshad R Patel
*Assistant Examiner* — Tran M Tran
(74) *Attorney, Agent, or Firm* — Kwan & Olynick LLP

(57) ABSTRACT

Systems, methods, and apparatus provide integration of microscopic imaging and liquid chromatography-mass spectrometry on a microfluidic device. In one aspect, an apparatus includes a first wafer, a second wafer, and an emitter. The emitter is disposed between the first wafer and the second wafer. The first wafer defines a sample input hole. The first wafer and the second wafer define a first channel, the first channel including a first end and a second end. The first end of the first channel is proximate the sample input hole. The first channel is configured to contain separation media. The second end of the first channel is proximate the emitter.

16 Claims, 13 Drawing Sheets

Related U.S. Application Data

(60) Provisional application No. 61/735,833, filed on Dec. 11, 2012.

(51) Int. Cl.
  G01N 30/60 (2006.01)
  G01N 30/72 (2006.01)
  B01L 3/00 (2006.01)
  G01N 30/88 (2006.01)

(52) U.S. Cl.
  CPC ..... G01N 30/7233 (2013.01); G01N 30/7266 (2013.01); H01J 49/0431 (2013.01); *B01L 2300/069* (2013.01); *B01L 2300/0803* (2013.01); *B01L 2300/0816* (2013.01); *B01L 2300/0861* (2013.01); *B01L 2300/0867* (2013.01); *B01L 2300/0887* (2013.01); *G01N 2030/8813* (2013.01)

(56) References Cited

U.S. PATENT DOCUMENTS

| | | | | |
|---|---|---|---|---|
| RE36,350 E | * | 10/1999 | Swedberg | B01L 3/502707 204/451 |
| 6,167,910 B1 | * | 1/2001 | Chow | B01J 19/0093 137/526 |
| 6,438,279 B1 | * | 8/2002 | Craighead | G02B 6/136 356/246 |
| 6,499,499 B2 | * | 12/2002 | Dantsker | F16K 99/0001 137/1 |
| 6,600,558 B2 | * | 7/2003 | Ueno | G01N 21/0332 356/244 |
| 6,621,076 B1 | * | 9/2003 | van de Goor | H01J 49/04 250/288 |
| 6,748,978 B2 | * | 6/2004 | Pezzuto | F16K 99/0001 137/833 |
| 6,845,968 B2 | * | 1/2005 | Killeen | F15C 5/00 137/625.46 |
| 6,936,167 B2 | * | 8/2005 | Hobbs | G01N 30/466 210/143 |
| 7,007,710 B2 | * | 3/2006 | Heller | H01J 49/0018 137/15.01 |
| 7,077,175 B2 | * | 7/2006 | Yin | G01N 30/56 141/130 |
| 7,391,020 B2 | * | 6/2008 | Bousse | B05B 5/025 250/281 |
| 7,413,709 B2 | * | 8/2008 | Roitman | B01J 19/0093 422/504 |
| 7,541,578 B2 | * | 6/2009 | Weng | B01L 3/502707 239/695 |
| 7,811,452 B2 | * | 10/2010 | Yin | B01L 3/502738 210/198.2 |
| 8,022,361 B2 | * | 9/2011 | Wang | B82Y 15/00 239/548 |
| 8,413,603 B2 | * | 4/2013 | Craighead | B82Y 30/00 118/621 |
| 8,656,949 B2 | * | 2/2014 | Fourkas | B29C 33/3857 137/561 A |
| 9,006,648 B2 | * | 4/2015 | Ramsey | B05B 5/025 250/288 |
| 9,459,182 B2 | * | 10/2016 | Akiyama | B01L 3/0268 |
| 9,490,111 B2 | * | 11/2016 | Abell | H01J 49/16 |
| 9,752,978 B2 | * | 9/2017 | Kraiczek | G01N 33/54373 |
| 2002/0153046 A1 | | 10/2002 | Dantsker et al. | |
| 2003/0141392 A1 | * | 7/2003 | Nilsson | H01J 49/167 239/690 |
| 2004/0067578 A1 | | 4/2004 | Axelsson | |
| 2004/0156753 A1 | | 8/2004 | Roitman et al. | |
| 2006/0022130 A1 | * | 2/2006 | Bousse | H01J 49/0018 250/288 |
| 2007/0116609 A1 | * | 5/2007 | Baeuerle | B01L 3/502715 422/400 |
| 2008/0041475 A1 | | 2/2008 | Fourkas et al. | |
| 2008/0213912 A1 | | 9/2008 | Randall et al. | |
| 2008/0235948 A1 | | 10/2008 | Bousse et al. | |
| 2010/0210008 A1 | | 8/2010 | Strand et al. | |
| 2011/0048945 A1 | | 3/2011 | Harrison et al. | |
| 2014/0065034 A1 | * | 3/2014 | Zheng | G01N 30/6095 422/502 |
| 2014/0110661 A1 | | 4/2014 | Wang et al. | |

OTHER PUBLICATIONS

Mao et al., Multinozzle Emitter Array Chips for Small-Volume Proteomics, Anal. Chem., 2013, 85 (2), pp. 816-819.
MSCAL 2013: Preliminary Conference Program, The Association for Mass Spectrometry: Applications to the Clinical Lab, published on-line Nov. 19, 2012.
Kim et al., Microfabricated Monolithic Multinozzle Emitters for Nanoelectrospray Mass Spectrometry, Anal. Chem. 2007, 79, 3703-3707.
Mao et al., Multinozzle Emitter Arrays for Nanoelectrospray Mass Spectrometry, Anal Chem. 2011, 83, 6082-6089.

* cited by examiner

MICROFLUIDIC DEVICES FOR LIQUID CHROMATOGRAPHY-MASS SPECTROMETRY AND MICROSCOPIC IMAGING

RELATED APPLICATIONS

This application is a continuation of International Application No. PCT/US2013/073022, filed Dec. 4, 2013, which claims priority to U.S. Provisional Patent Application No. 61/735,833, filed Dec. 11, 2012, both of which are herein incorporated by reference. This application is related to U.S. Pat. No. 8,022,361 and to International Application No. PCT/US2012/45082, both of which are herein incorporated by reference.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure is related to microfluidic devices, and more particularly to microfluidic devices for liquid chromatography-mass spectrometry and microscopic imaging.

BACKGROUND

Given that the proteome reflects the physiological and pathological states of a patient, proteomics is a powerful tool for early diagnostics of diseases and monitoring of therapeutic responses. The majority of current protein assays in clinical settings are based on enzyme-linked immunosorbent assay (ELISA) immunoassays, which require high-quality antibodies and are hard to achieve with high multiplexing (e.g., greater than 10) due to the cross-reactivity of antibodies. Mass spectrometry (MS) measures the mass-to-charge ratio of charged species, and has become an enabling technology for proteomics. Aside from de novo identification of target proteins, MS has advantages over ELISA for detecting protein mutations, modification, truncations, and adductations, for example. Once combined with the liquid chromatography (LC), LC-MS enables separation, identification, characterization, and quantitation of complex mixtures of proteins and peptides. However, the penetration of MS into the in vitro diagnostics market, particularly for clinical proteomics, has remained low. Key challenges remain for an MS-based platform to achieve robustness, sensitivity, and throughput comparable to those of ELISA for analysis of small-volume biospecimens such as blood and urine.

SUMMARY

High-throughput multiplexed proteomics of small-volume biospecimens may generate new opportunities in theranostics. Achieving parallel top-down and bottom-up mass spectrometry analyses of target proteins using a unified apparatus may improve proteome characterization. A novel silicon-based microfluidic device, a multinozzle emitter array chip (MEA chip), to be used as a new platform for small-volume proteomics using liquid chromatography-nanoelectrospray ionization mass spectrometry (LC-nanoESI-MS), is disclosed herein. Parallel, on-chip, and on-line LC-MS analysis of hemoglobin and its tryptic digests directly from microliters of blood, achieving a detection limit of less than 5 red blood cells, has been demonstrated. The MEA chip may enable clinical proteomics of small-volume samples.

In one aspect, a 24-plex multinozzle emitter array chip (MEA chip) includes 24 substantially identical units/channels on a two-layer 4-inch silicon substrate. Each unit/channel contains a sample input hole for sample injection, a LC channel for sample separation, and a multinozzle emitter for MS. The MEA chip may include through-holes designed for filling hardware (e.g., screws) during assembly. Media (e.g., beads) coated with a desired chemistry may be packed in the LC channel (approximate dimensions, length×width×depth: 5 cm×200 microns×200 microns). Frits may be used to retain the media inside the LC channel. All LC channels and emitters may be disposed between the two silicon substrates.

In another aspect, an imaging-mass spectrometry (iMS) chip may include a three-layer silicon-silicon-glass structure that monolithically integrates several components on a single chip. Multinozzle emitters are disposed between two silicon layers. All the other components including a cell trap chamber, enrichment and separation channels, and reservoirs for fluidic controls are disposed between the silicon and glass layers. The glass layer or cover plate provides a transparent window for imaging cell capture, manipulation, and processing.

In another aspect, an apparatus includes a first wafer, a second wafer, and an emitter. The first wafer defines a sample input hole. The first wafer and the second wafer define a first channel. The first channel includes a first end and a second end, the first end of the first channel proximate the sample input hole. The first channel is configured to contain separation media. The emitter is disposed between the first wafer and the second wafer, the second end of the first channel proximate the emitter.

In some embodiments, the first wafer and the second wafer both include silicon wafers. In some embodiments, the second end of the first channel includes a frit configured to retain separation media in the first channel. In some embodiments, the apparatus further includes separation media disposed in the first channel, with the separation media including a coating configured for separation of a sample into specific molecules. In some embodiments, the apparatus further includes separation media disposed in the first channel, with the separation media including beads, the beads being substantially spherical and having a diameter of about 1 micron to 50 microns.

In some embodiments, the apparatus further includes one or more channels, in addition to the first channel, forming a plurality of channels. In some embodiments, the first wafer and the second wafer are each substantially circular, with the plurality of channels being arranged about an axis of the first wafer and the second wafer. In some embodiments, the one or more channels are substantially identical to the first channel.

In some embodiments, the first channel has a cross-section of about 100 microns to 300 microns by about 100 microns to 300 microns. In some embodiments, the first channel has a length of about 3 centimeters to 15 centimeters.

In some embodiments, the emitter includes a first silica nozzle extending from a larger silica base tube, and with the first silica nozzle being a first nanotube or a first microtube. In some embodiments, walls of the first silica nozzle and the larger silica base tube form a monolithic whole. In some embodiments, the emitter further includes a second silica nozzle extending from the larger silica base tube, with the second silica nozzle being a second nanotube.

In some embodiments, the first wafer and the second wafer include through vias configured to allow fastening hardware to pass through the first wafer and the second wafer. In some embodiments, the sample input hole has dimensions of about 500 microns to 1.5 millimeters. In some embodiments, in the sample input hole is a through via in the first wafer.

In another aspect, a system includes a first wafer, a second wafer, an emitter, a wire, a metal plate, a polymer plate, and fastening hardware. The first wafer defines a sample input hole. The first wafer and the second wafer define a first channel. The first channel includes a first end and a second end, the first end of the first channel proximate the sample input hole. The first channel is configured to contain separation media. The emitter is disposed between the first wafer and the second wafer, the second end of the first channel proximate the emitter. The wire is in electrical contact with the first wafer, and the wire is configured to transmit a high voltage. The second wafer is in contact with the metal plate. The first wafer is in contact with the polymer plate. The first wafer and the second wafer further include through vias configured to allow the fastening hardware to pass through the first wafer and the second wafer. The fastening hardware is configured to connect the polymer plate to the metal plate with the first wafer and the second wafer disposed between the polymer plate and the metal plate and to apply a force to hold the first wafer against the second wafer.

In some embodiments, the metal plate includes a steel plate. In some embodiments, the polymer plate includes a polyether ether ketone (PEEK) plate.

In another aspect, an apparatus includes an emitter, a first wafer, a second wafer, and a transparent wafer. The first wafer and the second wafer define a sample input hole and a first exit channel having a first end and a second end. The emitter is disposed between the first wafer and the second wafer, the second end of the first exit channel proximate the emitter. The second wafer and the transparent wafer define a first channel having a first end and a second end, the first end of the first channel proximate the sample input hole, the second end of the first channel proximate the first end of the first exit channel. The first channel is configured to contain separation media.

In some embodiments, the transparent wafer includes a glass wafer. In some embodiments, the first wafer and the second wafer both include silicon wafers.

In some embodiments, the apparatus further includes separation media disposed in the first channel, with the separation media including a coating configured for separation of a sample into specific molecules. In some embodiments, the apparatus further include separation media disposed in the first channel, with the separation media including beads, the beads being substantially spherical and having a diameter of about 1 micron to 50 microns.

In some embodiments, the apparatus further includes one or more channels and exit channels, in addition to the first channel and first exit channel, forming a plurality of channels and exit channels. In some embodiments, the first wafer, the second wafer, and the transparent wafer are each substantially circular, with the plurality of channels and exit channels being arranged about an axis of the first wafer, the second wafer, and the transparent wafer. In some embodiments, the one or more additional channels and exit channels are substantially identical to the first channel and the first exit channel.

In some embodiments, the first channel includes a first section and a second section, the first section having a different cross-section than the second section.

In some embodiments, the emitter includes a first silica nozzle extending from a larger silica base tube, the first silica nozzle being a first nanotube or a first microtube. In some embodiments, walls of the first silica nozzle and the larger silica base tube form a monolithic whole. In some embodiments, the emitter further includes a second silica nozzle extending from the larger silica base tube, the second silica nozzle being a second nanotube.

Details of embodiments of the subject matter described in this specification are set forth in the accompanying drawings and the description below. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

Introduction

The design, fabrication, and applications of MEA chips (e.g., a 24-plex MEA chip) for on-chip and on-line LC-nanoESI-MS analysis of low-volume samples (e.g., whole blood samples) is described herein. The MEA chip is built on advances in developing the silicon-based microfabricated monolithic multinozzle emitters ($M^3$ emitters) and MEA chips for nanoelectrospray MS. These devices collectively offer a solution to the longstanding issue of the efficient coupling between silicon microfluidic chips and ESI-MS, and pave the way for large-scale integration on microfluidic chips for MS-based proteomics. Previous MEA chips, which are described in International Application No. PCT/US12/45082, achieved both high-sensitivity (e.g., via multinozzle emitters) and high-throughput (e.g., via multiple channels) MS on a single silicon microfluidic chip. However, proteins and peptides were separated by off-chip LC columns, and the fluidic interface was not robust enough for automatic control of high-throughput multiplexed proteomics. The new MEA chip described herein addresses these issues.

MEA Chip Configured for Liquid Chromatography-Mass Spectrometry

Figure 1A:
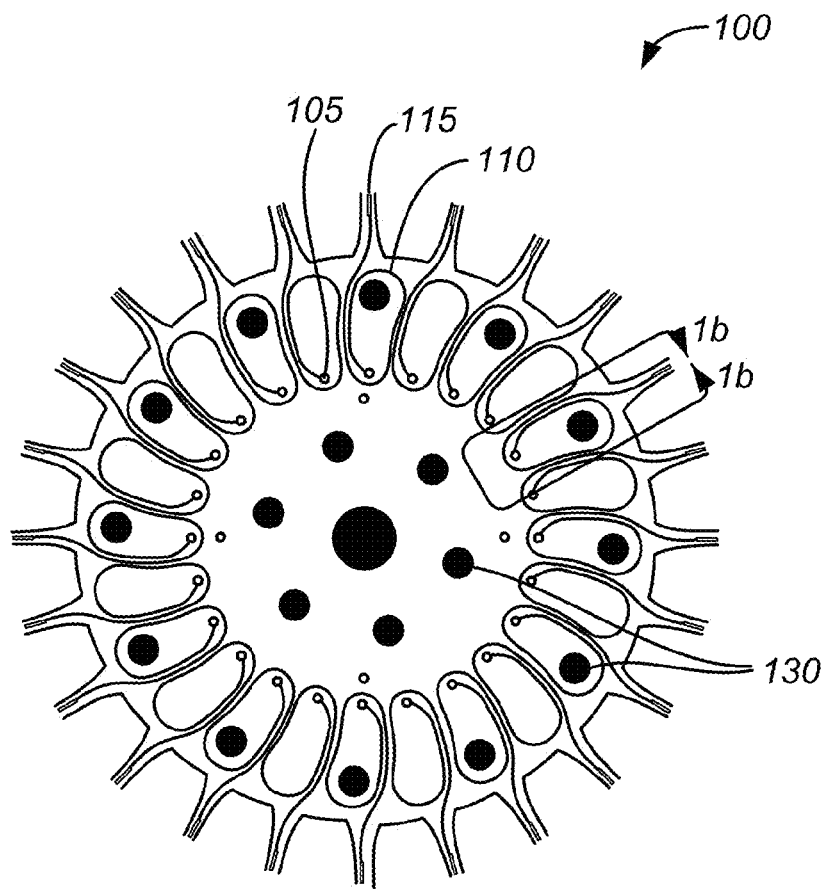
FIGS. 1A-1D show examples of schematic illustrations and a photograph of a multinozzle emitter array (MEA) chip and a MEA chip assembly.
Figure 1B:
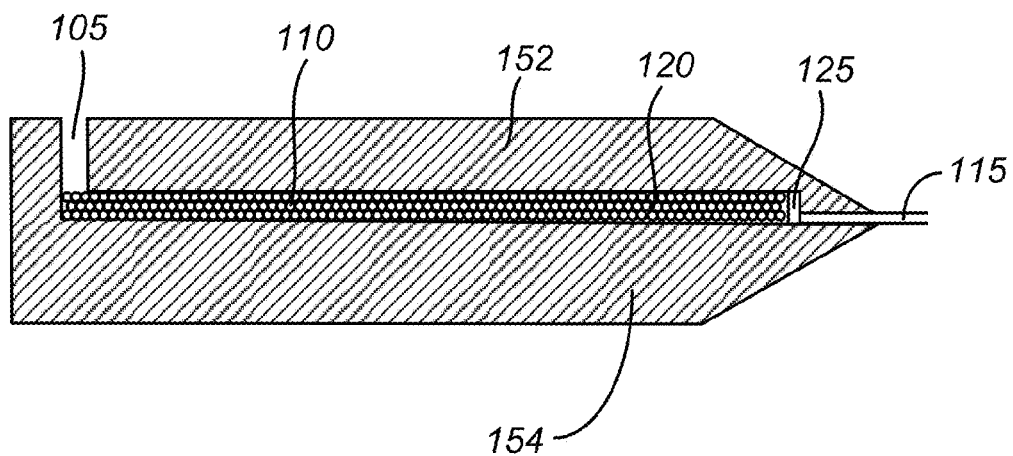

FIGS. 1A and 1B show examples of schematic illustrations of a MEA chip. FIG. 1A shows an example of a top-down schematic illustration of the MEA chip, and FIG. 1B shows an example of a cross-sectional schematic illustration of a channel of the MEA chip.

As shown in FIGS. 1A and 1B, a MEA chip 100 includes a plurality of channels. Each channel includes a sample input hole 105, a liquid chromatography channel 110, and an emitter 115. In some embodiments, the liquid chromatography channel 110 includes portions of the channel that are not the sample input hole 105 or the emitter 115. A first end of the liquid chromatography channel 110 is proximate and in fluid communication with the sample input hole 105. A second end of the liquid chromatography channel 110 is proximate and in fluid communication with the emitter 115. By the elements of the channel being in fluid communication or connected with one another, a sample (e.g., a liquid sample) may be introduced into the channel through the sample input hole 105, flow though the liquid chromatography channel 110, and exit the MEA chip 100 though the emitter 115. In some embodiments, each channel of the plurality of channels is substantially identical.

The MEA chip 100 is fabricated from two wafers, a first wafer 152 and a second wafer 154. In some embodiments, the emitter 115 may be disposed between the two wafers 152 and 154. In some embodiments, the first wafer 152 and the second wafer 154 may include silicon wafers. In some embodiments, the first wafer 152 and the second wafer 154 may include semiconductor wafers or other materials capable of conducting electricity. The first wafer 152 and the second wafer 154 define a plurality of channels. The channels shown in FIG. 1A include curves, but the channel shown in FIG. 1B is linear, for ease of depiction. The channel shown in FIG. 1B includes the sample input hole 105 and the emitter 115. As further shown in FIG. 1B, the channel includes separation media 120 and a frit 125.

In some embodiments, the sample input hole 105 may have dimensions of about 500 microns to 1.5 millimeters (mm), or about 1 mm. For example, when the sample input hole 105 is circular, the sample input hole 105 may have a diameter of about 500 microns to 1.5 mm, or about 1 mm. In some embodiments, a channel may have a substantially square cross section, a substantially rectangular cross section, a substantially circular cross section, an oval cross section, or another shaped cross section. In some embodiments, when a channel has a substantially square cross section, the dimensions of the cross section may be about 100 microns to 300 microns by about 100 microns to 300 microns, or about 200 microns by about 200 microns. A channel may have a length of about 3 centimeters (cm) to 15 cm, about 3 cm to 7 cm, or about 5 cm. A channel having a short length will allow a fluid to flow through the channel more quickly. A channel having a longer length may allow for better separation of molecules or chemical compounds in the liquid chromatography channel 110.

The separation media 120 may include solid particles (e.g., silica, polymers, or sorbents) configured to separate a sample into molecular and/or chemical constituents when the sample is forced through the channel under high pressure. In some embodiments, the separation media 120 may include beads, with the beads including a coating configured for separation of the sample into specific molecules or chemical compounds. In some embodiments, the beads may be substantially spherical and have a diameter of about 1 micron to 50 microns, about 3 microns to 7 microns, or about 5 microns. In some embodiments, the liquid chromatography channel 110 proximate the sample input hole 105 may include separation media 120 configured for protein enrichment and digestion, and the liquid chromatography channel 110 proximate the emitter 115 may include separation media 120 configured for peptide separation, protein separation, and small molecule (e.g., metabolites) separation.

The frit 125 is configured to keep the separation media 125 from flowing into the emitter 115. Thus, the opening in the frit 125 is smaller than the sizes of the constituents of the separation media 120. In some embodiment, the frit 125 may include features fabricated in the first wafer 152, the second wafer 154, or both the first and the second wafers to reduce the size of the liquid chromatography channel 110 so that the separation media 125 cannot flow through or past the frit 125. Dimensions of an opening of the frit 125 (e.g., a diameter of the opening of the frit) may be about 1 micron to 3 microns, or about 2 microns.

In some embodiments, the emitter 115 may include a first silica nozzle (not shown) extending out from a larger silica base tube (not shown). In some embodiments, the first silica nozzle may be a first nanotube. In some embodiments, the first silica nozzle may be a first microtube. In some embodiments, the walls of the first silica nozzle and the larger silica base tube may form a monolithic whole. In some embodiments, the emitter may further include a second silica nozzle extending out from the larger silica base tube, and the second silica nozzle may be a second nanotube. The silica nozzle(s) may be used for nanoelectrospray MS identification and quantitation of proteins and peptides. When more than one silica nozzle is included in the emitter, the silica nozzles may form a multinozzle emitter. The number of silica nozzles included in the emitter may be 1 nozzle, 4 nozzles, 10 nozzles, or 50 nozzles, for example.

In some embodiments, nozzles associated with the emitter 115 may have a cross-sectional area of about 10 microns×10 microns, a length of about 150 microns, and wall thickness of about 0.5 microns. In some embodiments, the protruding end of an emitter may be sharpened, leaving it with an angle of about 20°; that is, material of the emitter may be removed to form a tip ending with a nozzle or nozzles. This may enhance the electric fields at the nozzle end. Emitters and associated nozzles are further described in U.S. Pat. No. 8,022,361, which was previously incorporated by reference.

Figure 1C:
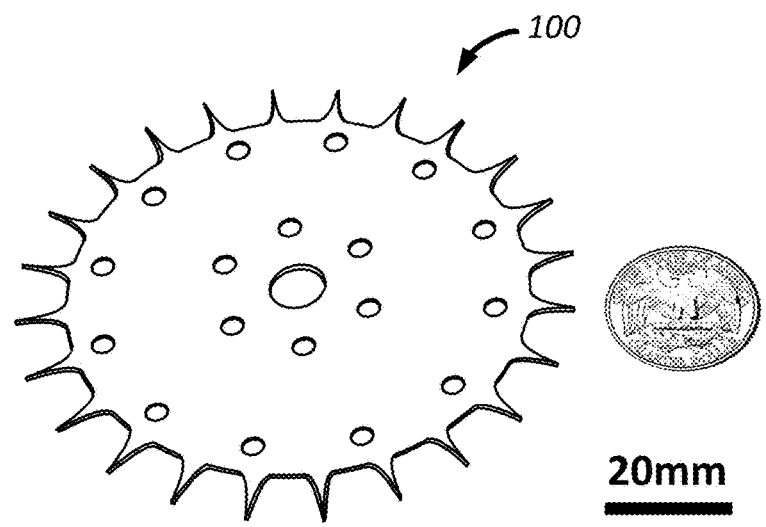

FIG. 1C shows a photograph of a 24 channel MEA chip with a United States quarter for size comparison. While the MEA chip 100 shown in FIGS. 1A and 1C includes 24 channels (i.e., sample input holes, liquid chromatography channels, and emitters), a MEA chip may include any number of channels. For example, a MEA chip may include 1 channel, 2 channels, 24 channels, 96 channels, or 384 channels. Further, the MEA chip 100 is shown in FIGS. 1A and 1C as being substantially circular (i.e., the first wafer 152 and the second wafer 154 are each substantially circular), which the plurality of channels being arranged about an axis of the first wafer 152 and the second wafer 154. Other configurations of an MEA chip are possible, however.

In some embodiments, the MEA chip 100 may not include the separation media 120 and the frit 125 disposed in the liquid chromatography channel 110. Such embodiments may be used for direct infusion of a sample into a mass spectrometer. In some embodiments, some channels of a MEA chip may not include the separation media and the frit disposed in the liquid chromatography channels, and other channels of the MEA chip may include the separation media and the frit disposed in the liquid chromatography channels. Different configurations of a MEA chip are possible, and the configuration may be tailored to the analyses desired to be performed.

The MEA chip 100 may be mounted in a system (e.g., a fluidic manifold assembly) for use of the MEA chip. In some embodiments, to incorporate the MEA chip 100 into an experimental system, the first wafer 152 and the second wafer 154 of the MEA chip 100 may include through vias 130 configured to allow fastening hardware to pass through the first wafer and the second wafer. In some embodiments, such fastening hardware may include screws, bolts, and alignment pins to incorporate the MEA chip 100 into an experimental system. For example, four alignment pins may be implemented, each on a quarter of the assembly.

Figure 1D:
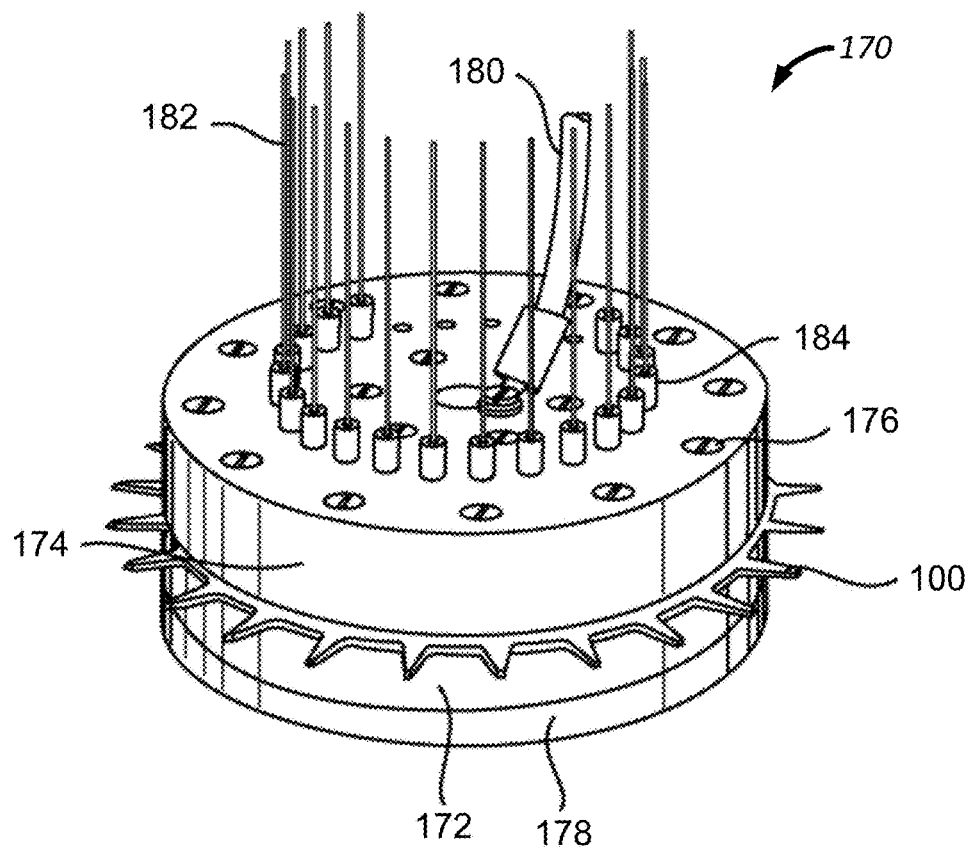

FIG. 1D shows a schematic illustration of a MEA chip assembly. In some embodiments, a MEA chip assembly 170 may include two clamping plates. The two clamping plates may include a metal plate 172 in contact with the second wafer and a polymer plate 174 in contact with the first wafer of the MEA chip 100. In some embodiments, the metal plate 172 may include a steel plate. In some embodiments, the polymer plate 174 may include a polyether ether ketone (PEEK) plate. In some embodiments, the MEA chip assembly 170 may include a gasket (not shown) between the MEA chip and a clamping plate or plates to aid in preventing fluid leakage. In some embodiments, the face of the metal plate 172 in contract with the MEA chip 100 may be covered with a polyimide film (e.g., Kapton tape) for electrical insulation.

Fastening hardware 176 may be used to connect the polymer plate 174 to the metal plate 172 with the MEA chip 100 disposed between the polymer plate and the metal plate. The metal plate and the polymer plate may apply a force holding the first wafer against the second wafer when the MEA chip 100 is in operation. In some embodiments, another polymer plate 178 may be in contact with the metal plate 172. The polymer plate 178 may provide an interface or an attachments point to a motorized rotation stage (described further with respect to FIGS. 3A and 3B, below). In some embodiments, the polymer plate 178 may be a PEEK plate or an acrylic plate.

Further, the MEA chip assembly 170 may include a wire/cable 180 in electrical contact with the first wafer. The wire may be configured to transmit a high voltage to the MEA chip 100 for electrospray. In some embodiments, the wire may be a palladium wire. Capillary tubing 182 and associated fittings 184 also may be associated with the MEA chip assembly. For example, the polymer plate 174 may include threaded ports (e.g., 24 threaded ports) for fittings 184 (e.g., Upchurch fittings) configured to provide leak-free connections with the capillary tubing 182 for delivering solvent gradients from a nanoflow source to channels of a MEA chip. Further description of a MEA chip assembly in a system configured for use of a MEA chip is given with respect to FIGS. 3A and 3B, below.

The MEA chips may be designed using a software package. The fabrication process for a MEA chip may be similar to what has described in Mao, P.; Wang, H. T.; Yang, P.; Wang, D. *Anal Chem.* 2011, 83, 6082-6089, which is herein incorporated by reference, for the first-generation MEA chips. As shown in FIG. 1B, all channels on the chip may be created between the two silicon wafers. A 2 micron frit may be implemented at the end of channels to retain the separation media (e.g., beads). The separation media may include, for example, Zorbax SB-C18 5 micron beads (pore size of 80 Å, from Agilent Technologies, of Santa Clara, Calif.).

When the separation media include beads, the beads may be placed in a channel by first suspending them in an alcohol (e.g., 2-propanol) and sonicating this mixture to form a slurry of mono-dispersed particles. Then, the slurry of particles may be forced into a channel of the MEA chip through a sample input hole by a pressurized gas (e.g., greater than about 500 psi helium). The pressure may be removed after about 20 minutes and the system may be slowly depressurized for about one hour before switching to atmospheric pressure. The quality and reproducibility of bead packing using such a process was confirmed by monitoring the backpressure of an LC channel under a constant flow rate (e.g., 1 µL/min), and the efficiency of LC separation in the LC channel was validated by the LC-MS analysis of GFP and BSA tryptic digests.

Experiments Using a MEA Chip

The following description of experiments using a MEA chip are intended to be examples of the embodiments disclosed herein, and are not intended to be limiting. The performance of emitters was validated for MS analysis of standard proteins and peptides. Electrosprays from emitters with varying numbers of nozzles were demonstrated, and confirmed that the MS sensitivity using emitters was approximately proportional to the square root of the number of the spraying nozzles. FIGS. 2A-2H show the results of proof-of-principle experiments using a 24-plex MEA chip.

Figure 2A:
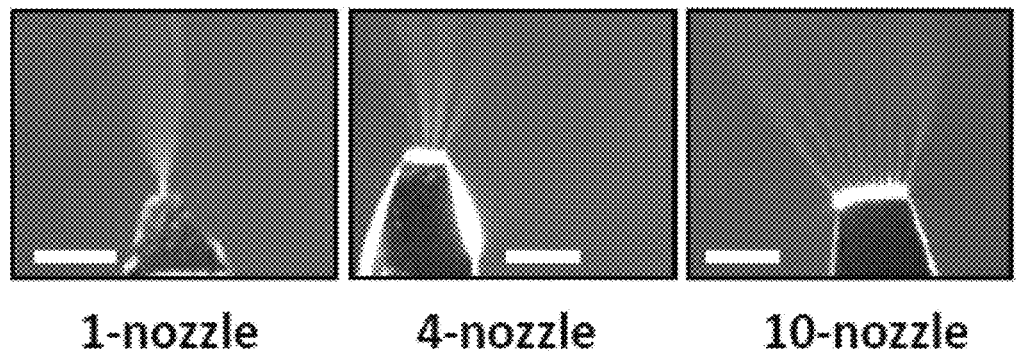
FIGS. 2A-2H show the results of proof-of-principle experiments using a 24-plex MEA chip.
Figure 2B:
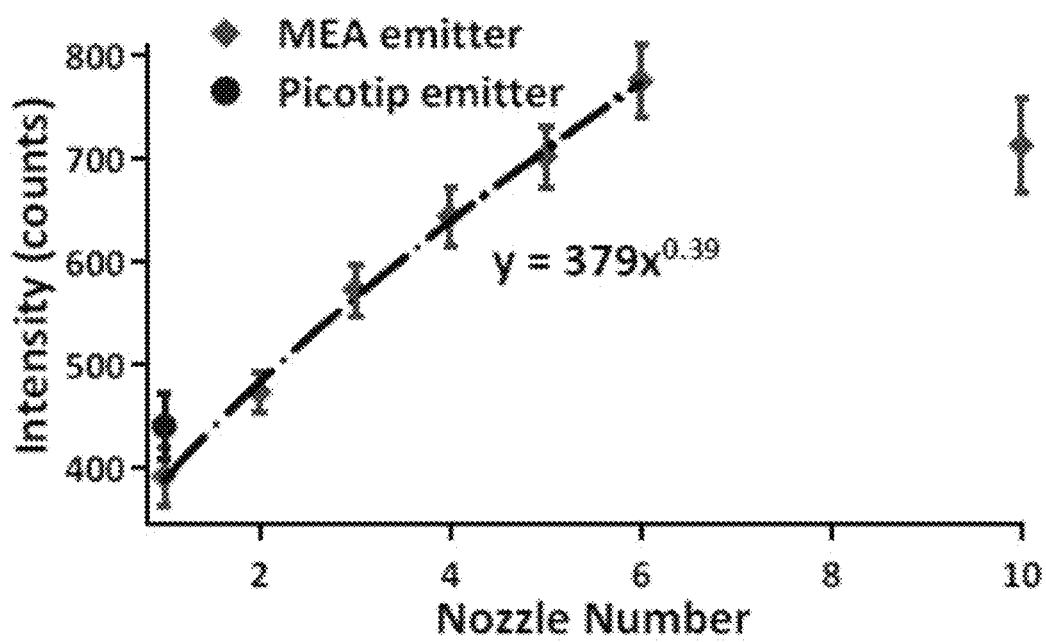

FIGS. 2A and 2B show the dependence of ESI-MS sensitivity on the nozzle number of emitters. FIG. 2A shows representative images for electrospray of 1-, 4-, and 10-nozzle emitters, scale bars are 500 microns. FIG. 2B shows the sensitivity dependence on nozzle numbers of emitters. A Picotip (New Objective, Inc., of Woburn, Mass.) emitter was used as a comparison. MS sensitivity of emitters using GFP (100 fmole/µL) illustrates a power-law relation to spraying nozzle numbers (1-6) with a power constant of 0.39. 10-nozzle data were excluded for curve fitting because of inefficient ion collection due to the existing MS ion cone.

The multinozzle emitters achieved sensitivity significantly higher than that of the commercial Picotip emitters. The 10-nozzle emitter, however, was an outlier. Without being bound to any theory, this was probably due to two factors. First, the maximum voltage (5 kV) provided by the mass spectrometer used in these experiments might not generate electric fields high enough to produce cone-jet mode spray for all 10 nozzles of the emitter uniformly. Second, ion collection and transmission by the Z-spray sample cone of the mass spectrometer was much less efficient for 10-nozzle emitters, because electrosprays were spread out significantly, resulting in a plume much larger in size than the MS cone inlet. Future implementation of a funnel-shaped sample cone for more efficient ion collection may further increase MS sensitivity for multinozzle emitters.

Figure 2C:
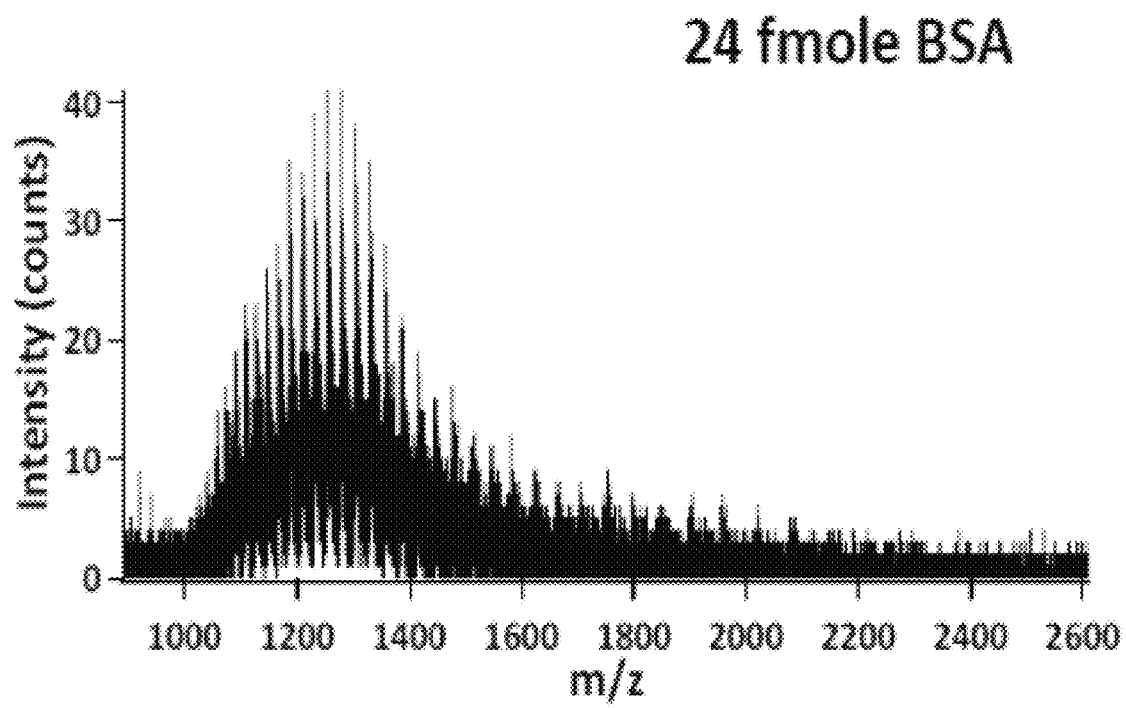
Figure 2D:
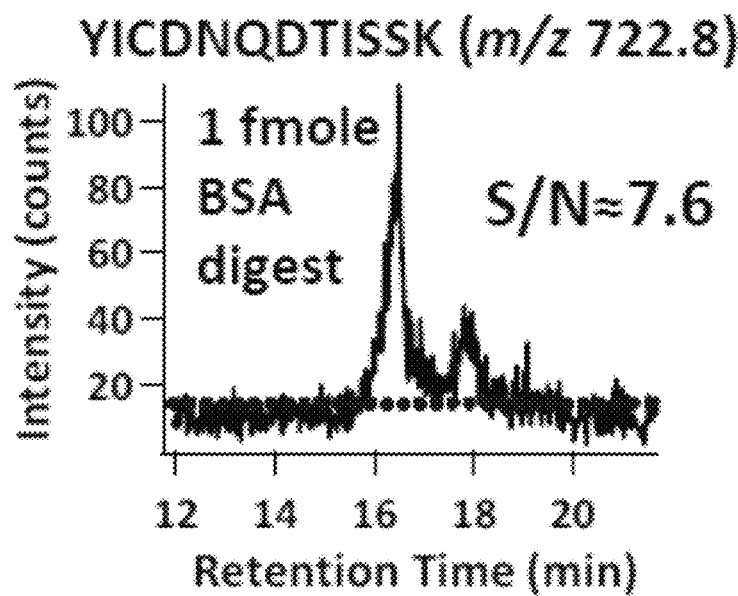
Figure 2E:
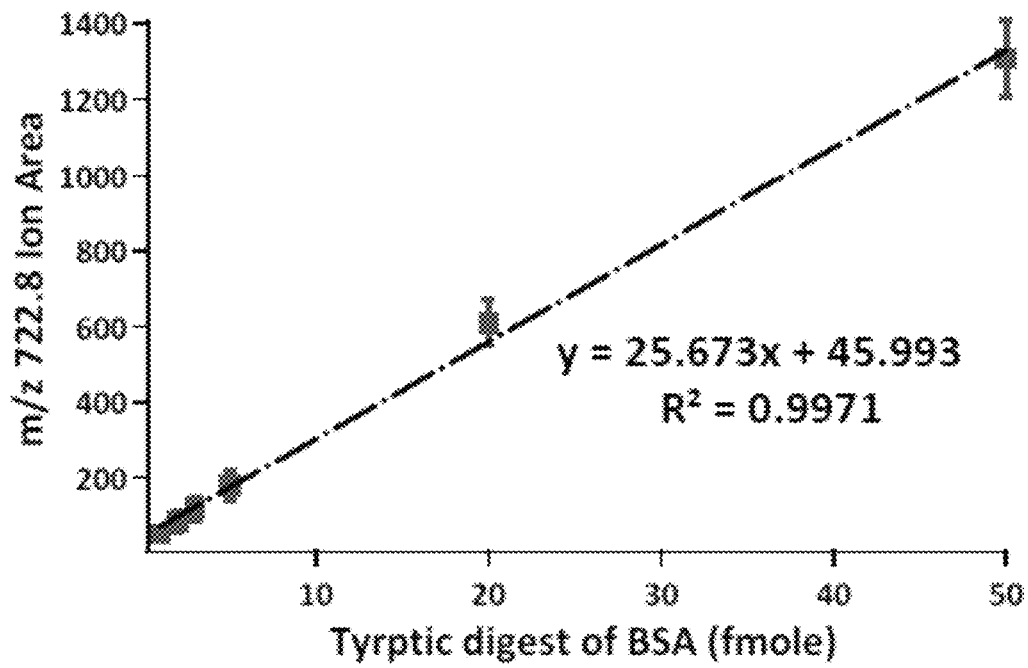

The performance of 24-plex MEA chips as a unified platform for parallel analysis of standard proteins and their tryptic peptides was validated. One unpacked channel for direct infusion MS analysis of full-length proteins was used, and another channel packed with C18 beads for LC-MS analysis of their tryptic digests. The reproducibility of on-chip LC-MS analysis using GFP was confirmed. The separation efficiency and detection sensitivity using BSA and its tryptic digests was tested (FIGS. 2C-2E). FIG. 2C shows a representative mass spectrum of 24 fmole BSA. High-sensitivity detection of full-length BSA (~24 fmole) using direct infusion MS analysis, and a limit of detection (LOD, signal-to-noise ratio S/N=3) of ~400 attomole (i.e., $10^{-18}$ mole) BSA tryptic digest for the m/z 722.8 ion (YICDNQDTISSK) using LC-MS/MS was achieved. A linear correlation between the LC-MS peak area and BSA digest concentration was observed (FIGS. 2D and 2E). The MS sensitivity of the MEA chips can be further improved by interfacing them with the latest mass spectrometers, which have the sensitivity for peptide detection and quantitation in the low attomole range.

Figure 2F:
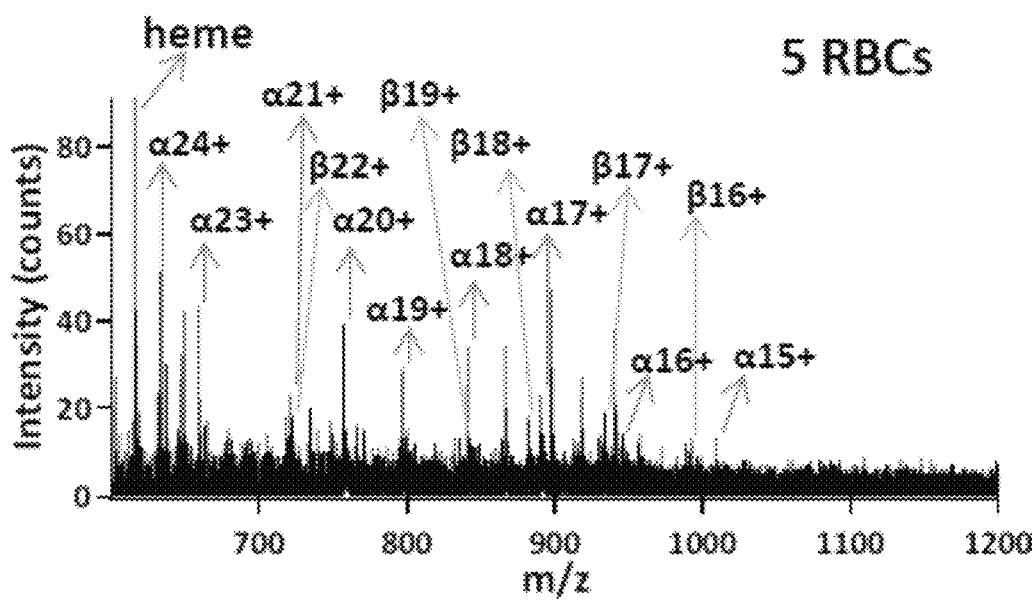
Figure 2G:
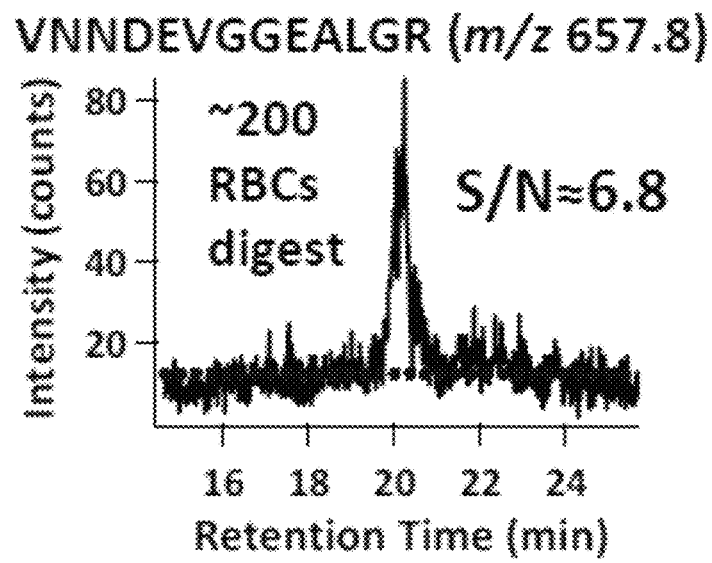
Figure 2H:
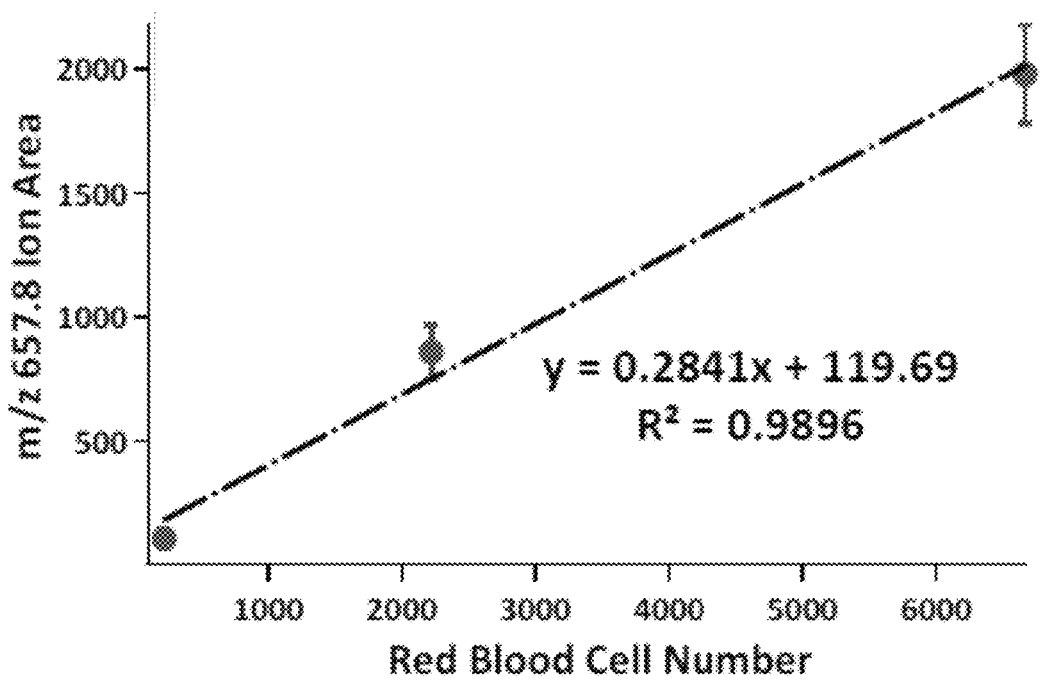

The performance of MEA chips for small-volume proteomic analysis of pooled human blood samples was also evaluated. The experiments started with less than 10 μl of whole blood. By direct infusion MS of the blood lysate, the heme group and several multiply-charged species of hemoglobin (Hb) α and β subunits from as little as 5 red blood cells (RBCs) were confidently detected (FIG. 2F). A LOD (S/N=3) of Hb tryptic digests from ~90 RBCs for the m/z 657.8 ion (VNNDEVGGEALGR) using LC-MS/MS was achieved (FIGS. 2G and 2H). A linear correlation between the LC-MS peak area and the number of lysed RBCs was observed (FIGS. 2G and 2H). Therefore, one of the immediate clinical applications of the MEA chips may be low-cost and high-throughput detection of Hb variants using a pinprick of blood in newborn screening. With both top-down and bottom-up MS analyses of Hb using extremely-small volumes of blood on a single device, the MEA chip platform is expected to have advantages in accuracy, resolution, and throughput for Hb analysis over the existing methods, including matrix-assisted laser desorption/ionization time-of-flight (MALDI-TOF) MS and direct infusion electrospray MS.

Preparation of Blood Cell Lysate and Trypsin Digestion.

A 10 μL aliquot of whole blood obtained from healthy donors (Innovative Research, Inc., of Novi, Mich.) was diluted in 1×PBS buffer to make cell suspensions of 1×10$^6$ cells per mL, as validated by Coulter Counter (Beckman Coulter, of Brea, Calif.). 100 μL of cell suspension (1×10$^5$ cells in total) was spun down in a centrifuge at a speed of 5,000 rpm. Supernatant was removed and precipitated cells at the bottom were lysed by freeze/thaw cycles using dry ice. For direct infusion MS analysis of proteins using unpacked channels on MEA chips, blood cell lysate was suspended in 50/50 acetonitrile/$H_2O$+0.1% formic acid and spun down in a centrifuge to precipitate cell lysate debris. The supernatant was collected and analyzed. The final concentration corresponded to proteins from a lysate of ~200 cells per μL.

For LC-MS analysis of tryptic peptides using channels packed with C18 beads, blood cell lysate was suspended in 25 mM ammonium bicarbonate and spun down to precipitate cell debris. The supernatant was collected and digested by sequencing grade modified porcine trypsin (Promega, of Santa Clara, Calif.) at a trypsin:protein ratio of 1:50 (w/w). The mixture was incubated at 37° C. overnight and afterwards 0.6 μL of 10% formic acid was added to stop digestion. The final sample concentration corresponded to proteins from lysate of ~2000 cells per μL. The sample was aliquoted and stored at −20° C. until further analysis.

On-Chip LC-MS/MS Analysis.

A capillary liquid chromatography system (CapLC) (Waters Corp., of Milford, Mich.) was used to deliver nanoflow for LC separation on the MEA chip. Peptide separation was performed at a flow rate of 300 nL/min using the same LC gradients as described in Mao, P.; Wang, H. T.; Yang, P.; Wang, D. *Anal Chem.* 2011, 83, 6082-6089, which is herein incorporated by reference. The sample was injected through an autosampler and LC-MS/MS was performed using on-chip LC channels. The most abundant peptide ions for each target protein were used for quantification. Extracted ion chromatograms were acquired to obtain peak areas for selected peptide ions. Peak areas were plotted against the concentrations of protein digests. BSA tryptic digests MS standard (Michrom Bioresources, Inc., of Auburn, Calif.) was used to validate the performance of on-chip LC-MS/MS analysis. The peptide ion YICDNQDTISSK (m/z 722.8) was selected for calibration and quantitation. The tryptic digests of hemoglobin (both α and β subunits) from RBCs in whole blood were analyzed by LC-MS/MS. The most abundant tryptic peptide ion VNNDEVGGEALGR (m/z 657.8) was from the hemoglobin β subunit, and selected for quantifying the number of RBCs. The limit-of-detection (LOD) was defined as the lowest concentration point of target proteins at which the signal-to-noise ratio (S/N) of surrogate peptides was at least 3. S/N was calculated by the peak apex intensity over the average background noise in a retention time region of ±5 min for target peptides.

Nanoelectrospray Mass Spectrometry.

All MS experiments were performed using a hybrid quadrupole/orthogonal Q-TOF API US mass spectrometer (Waters Corp., of Milford, Mich.). The MEA chip assembly was mounted on a rotation stage with an automatic motorized control, which was further attached to a XYZ translational stage (see FIGS. 3A and 3B, discussed below). The solvent was delivered to the on-chip channels from a nanoflow source through connecting tubing. An individual MEA chip emitter was positioned in front of the MS ion cone for nanoelectrospray in the Z spray geometry. A high voltage cable was connected to the center region of the silicon-based MEA chip via a metal wire, and provided up to 5 kV for electrospray. This connection strategy reduced tangling between the cable and capillary tubing and eliminated electric arcing during operation (including rotation) of the MEA chip assembly. The electrospray process was visualized and monitored using a Waters nanoflow camera kit equipped with a MLH-10 Zoom lenses (Computar, of Commack, N.Y.). Protein samples (BSA or hemoglobin from red blood cells) were analyzed using emitters by direct infusion using unpacked channels at a flow rate of 600 nL/min.

System Configured to Use a MEA Chip

Figure 3A:
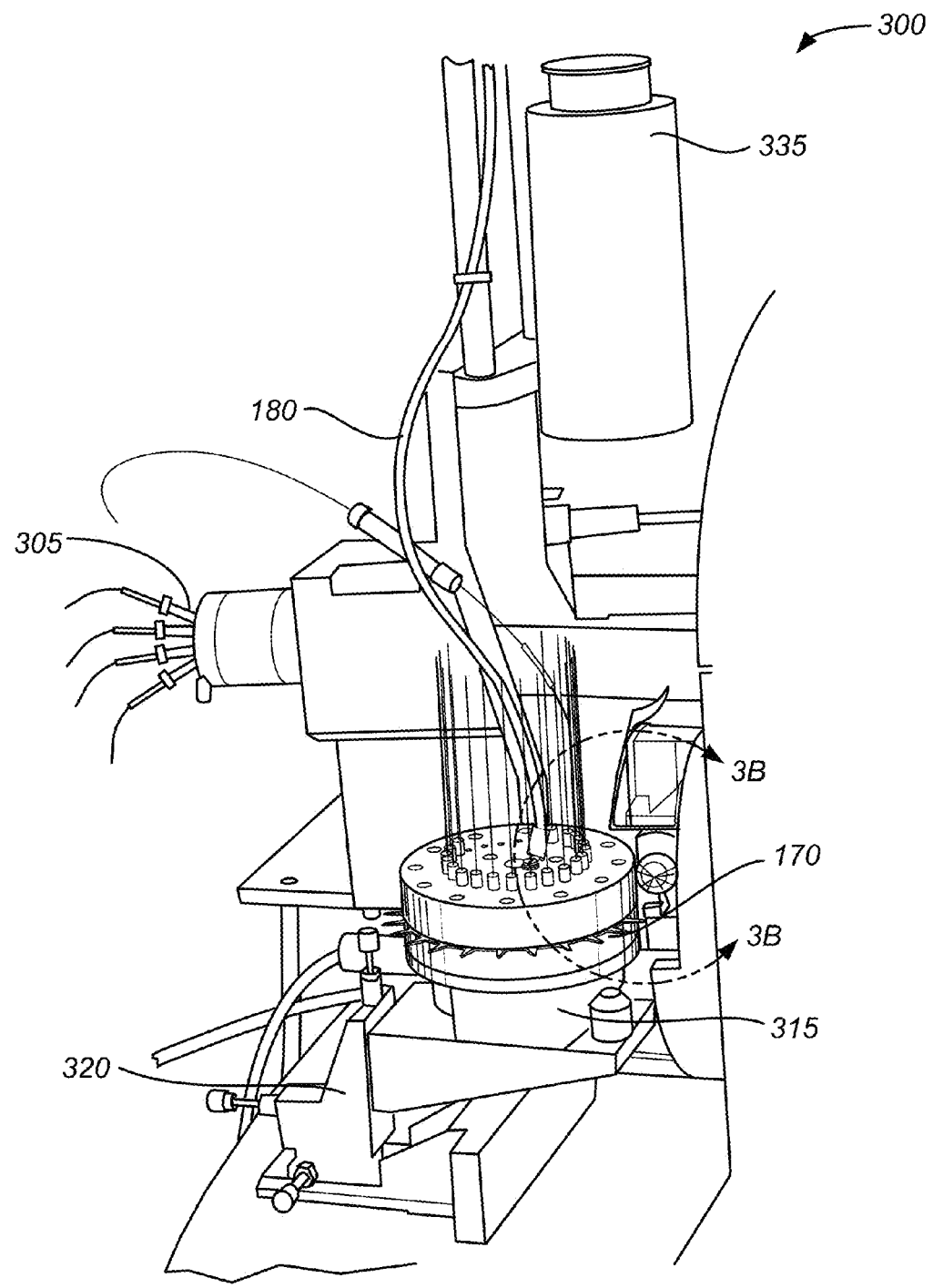
FIGS. 3A and 3B shows an example of a schematic illustration of a system configured for use of a 24-plex MEA chip.

To establish a robust and high-quality fluidic connection to sustain high pressure for on-chip LC separation, a manifold to mechanically assemble the MEA chip with capillary tubing that are connected to the outside nanoflow source may be used. FIG. 3A shows an example of a schematic illustration of a system configured for use of a 24-plex MEA chip. The system 300 includes a nanoflow source 305 configured to provide the solvent gradient flow into the MEA chip through tubing connections, a MEA chip assembly 170, a motorized rotation stage 315 (e.g., from Thorlabs, of Newton, N.J.), and a XYZ translation stage 320 configured to finely tune the position of a particular emitter towards a MS cone 325, a wire/cable 180 configured for high voltage supply, and a camera 335 configured to image the position and electrospray process of emitters. The MEA chip assembly 170 may be mounted to the motorized rotation stage 315 using the polymer plate 178 (described with respect to FIG. 1D) of the MEA chip assembly 170 (e.g., using a screw in a center hole).

Figure 3B:
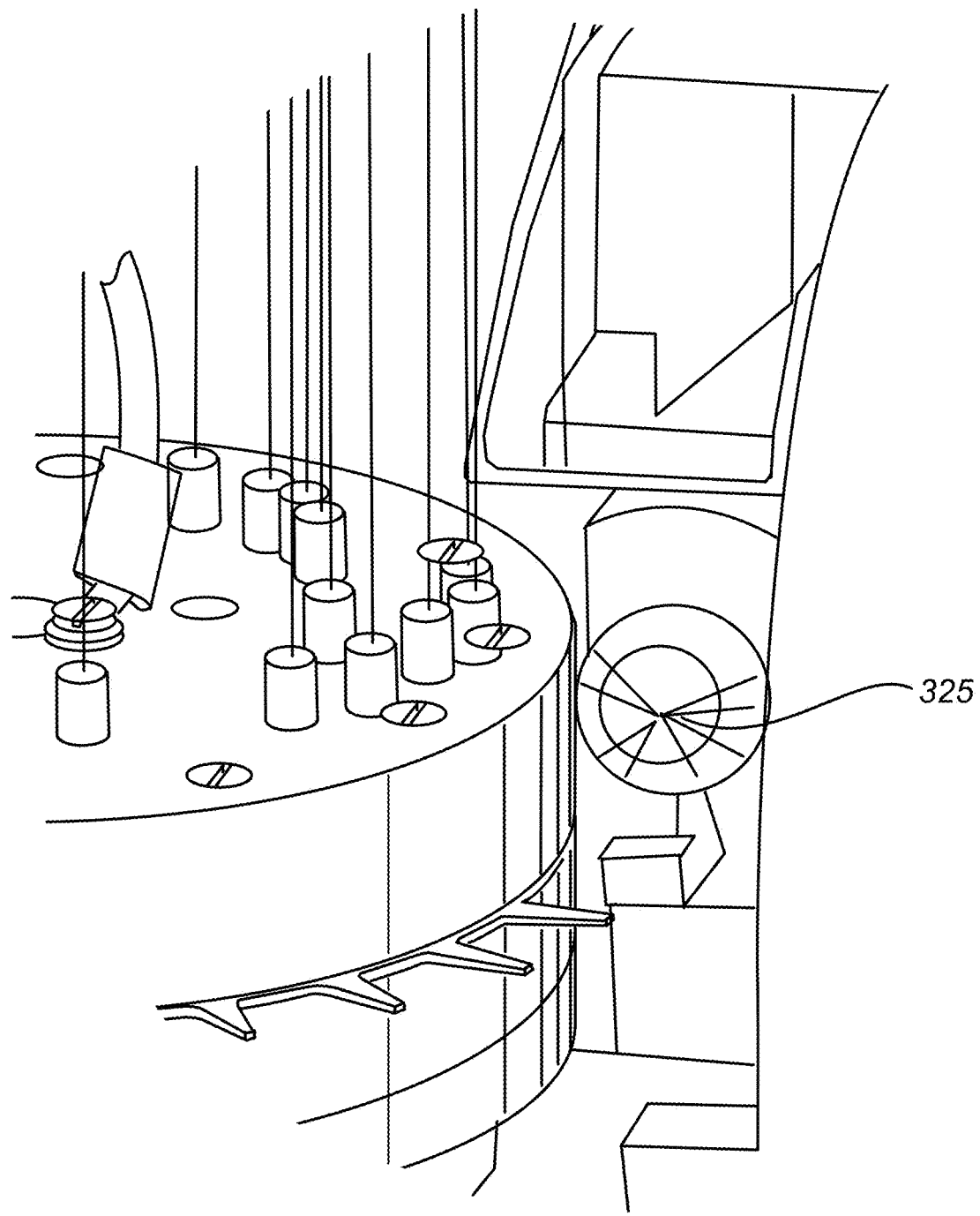

FIG. 3B shows the Z spray geometry of the emitters on the MEA chip assembly 170 relative to the MS cone 325 of a mass spectrometer (e.g., a Waters Q-TOF API US, Waters Corporation of Milford, Mass.).

No fluid leakage was observed for liquid flow under a pressure of up to about 1000 psi using the MEA chip assembly 170 as shown in FIGS. 1D and 3A.

iMS Chip Configured for Imaging and Liquid Chromatography-Mass Spectrometry

As noted above, mass spectrometry (MS) is the enabling technology for proteomics and metabolomics, and is typically used to measure biochemical compositions and metabolic states of a large population of cells. Single cell analysis, however, currently relies predominantly on microscopy-based bioimaging through optical and/or fluorescence signals that require in vivo or in vitro labeling. Recent developments in imaging mass spectrometry using MS signals, including secondary ion mass spectrometry (SIMS) imaging, matrix-assisted laser desorption ionization (MALDI) imaging, desorption electrospray ionization (DESI) imaging, and laser ablation electrospray ionization (LAESI) imaging, make single cell MS imaging possible. However, MS is a destructive technique and cannot be performed on live cells. The ability to directly image live cells (e.g., with and without stimulation), and perform mass spectrometry in situ for a small number of cells (e.g., down to a single cell), on a unified platform (e.g., an integrated microfluidic system), may open up new areas of biomedical research. Furthermore, this technique, i.e., imaging-mass spectrometry (iMS), can take advantage of new developments in both bioimaging (e.g., single-molecule and single-cell microscopy) and mass spectrometry (e.g., a multinozzle emitter array (MEA) chip), and can be realized in a high-throughput format with a lab-on-a-chip system.

Infrared light, for example, may be used for imaging with a MEA chip (i.e., a MEA chip including silicon or other semiconductor wafers). In some other embodiments, a MEA chip may include a glass wafer. With a MEA chip including a glass wafer, imaging may be performed with visible light or a shorter wavelength light (e.g., for fluorescent imaging), for example. Coupling bioimaging with mass spectrometry may enable single cell analysis at both cellular and molecular levels and thereby open up new areas of research.

For example, in some embodiments, an imaging mass spectrometry chip (iMS chip) may include an emitter, a first wafer, a second wafer, and transparent wafer. The first wafer may define a sample input hole. The first wafer and the second wafer may define an exit channel having a first end and a second end. The emitter may be disposed between the first wafer and the second wafer. The second end of the exit channel may be proximate and in fluid communication with the emitter. The second wafer and the transparent wafer may define a chromatography channel having a first end and a second end. The first end of the chromatography channel may be proximate and in fluid communication with the sample input hole, and the second end of the chromatography channel may be proximate and in fluid communication with the exit channel. The chromatography channel may be configured to contain media (e.g., separation media). In some embodiments, the transparent wafer may include a glass wafer. In some embodiments, the first wafer and the second wafer may both include silicon wafers. Additional features defined by the second wafer and the transparent wafer may allow for imaging of a sample.

Figure 4A:
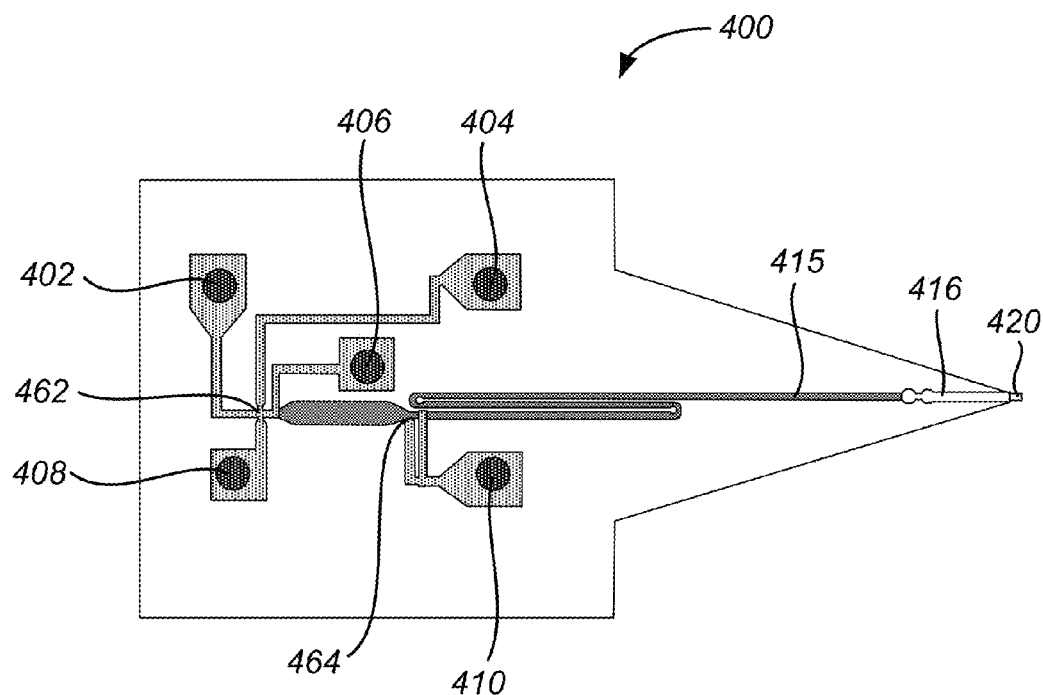
FIGS. 4A-4H show examples of schematic illustrations and photographs of an imaging-mass spectrometry (iMS) chip.
Figure 4B:
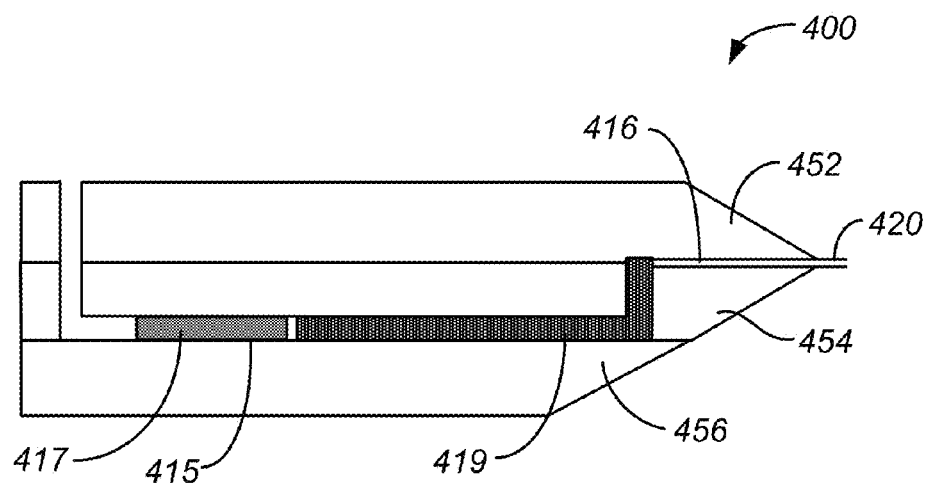

FIGS. 4A-4H show examples of schematic illustrations and photographs of an iMS chip. FIG. 4A shows an example of a top-down schematic illustration of the iMS chip. FIG. 4B shows an example of a cross-sectional schematic illustration of a channel of the iMS chip. In some embodiments, features of an iMS chip may be similar to features of a channel in an MEA chip, described above. For example, an iMS chip may include a sample input hole, a channel configured to contain media, and an emitter, which may be similar to the same features of a channel of a MEA chip. Additional features and capabilities of an iMS chip are described below.

As shown in FIGS. 4A and 4B, an iMS chip 400 includes a channel. The channel includes a plurality of sample input holes 402, 404, 406, and 408, a processing channel 415, an exit channel 416, and an emitter 420. A first end of the processing channel 415 is proximate and in fluid communication with the sample input holes 402, 404, 406, and 408. The input holes are used to inject individual samples onto the iMS chip for separation and analysis. A second end of the processing channel 415 is proximate and in fluid communication with a first end of the exit channel 416. A second end of the exit channel 416 is proximate and in fluid communication with the emitter 420. By the elements of the channel being in fluid communication or connected with one another, a liquid sample may be introduced into the channel through a sample input hole, flow through the processing channel 415 and the exit channel 416, and exit the iMS chip 400 though the emitter 420. The emitter 420 may be used for nanoelectrospray MS identification and quantitation of proteins and peptides, for example.

The iMS chip 400 is fabricated from three wafers, a first wafer 452, a second wafer 454, and a transparent wafer 456. In some embodiments, the first wafer 452 and the second wafer 454 may include silicon wafers. In some embodiments, the first wafer 452 and the second wafer 454 may include semiconductor wafers or other materials capable of conducting electricity. In some embodiments, the emitter 420 may be disposed between the first wafer 452 and the second wafer 454. In some embodiments, the transparent wafer 456 may include a glass wafer or a portion of a sheet of glass. The transparent wafer 456 may provide an imaging window that allows for real-time monitoring of cell manipulation and processing.

In some embodiments, the processing channel 415 includes an enrichment channel 417 and a liquid chromatography channel 419. The enrichment channel 417 and the liquid chromatography channel 419 are configured to contain media (e.g., ZORBAX SB-C18 5 micron beads). In some embodiments, the media may be used for protein enrichment and digestion, followed by peptide separation through on-chip liquid chromatography (LC).

In some embodiments, the channel also may be connected to an access hole 410. The access hole 410 may be used to fill the channel with media. For example, when the media includes particles of beads, the media may be mixed with a liquid (e.g., an alcohol, such as 2-propanol) and then forced into the channel though the access hole 410 using a pressurized gas (e.g., pressurized helium at about 250 psi).

In some embodiments, the iMS chip 400 may further include a plurality of frits 464. The plurality of frits 464 is configured to retain the media in the processing channel 415. In some embodiments, the iMS chip 400 may further include a cell trap 462. The cell trap 462 may be used for capturing cells of interest with high specificity and sensitivity. A cell trap may include obstacles with inter-obstacle distances smaller than a cell. For example, a micropillar array with inter-pillar distance smaller than a cell can be used for a cell trap. Alternatively, a cell trap may include a filter or filters with open pore sizes smaller than a cell. Cell traps are further described below with reference to FIGS. 5A and 5B.

Figure 4C:
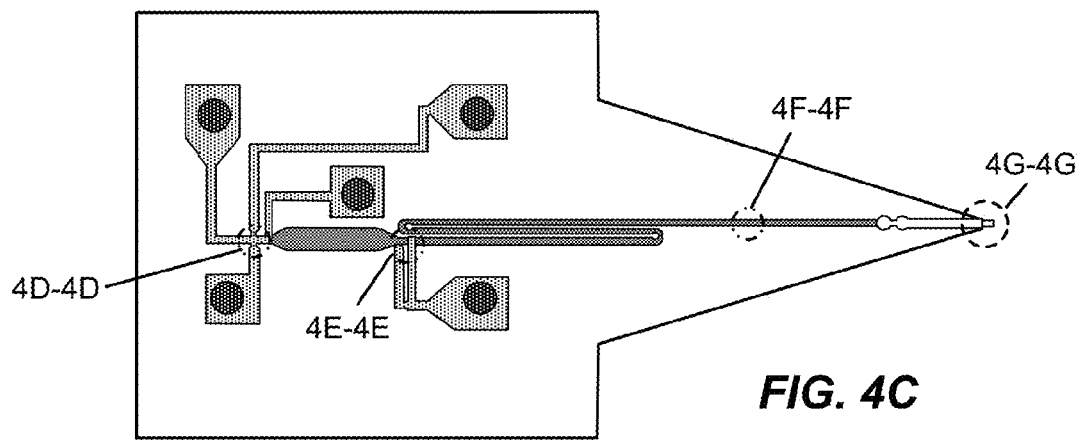
Figure 4D:
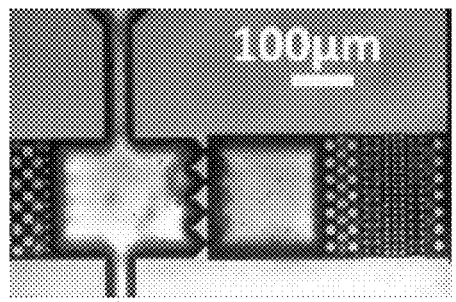
Figure 4E:
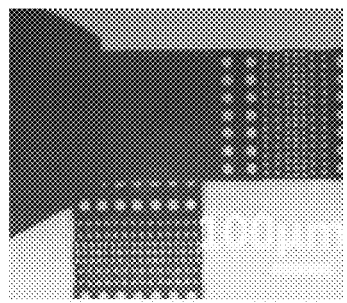
Figure 4F:
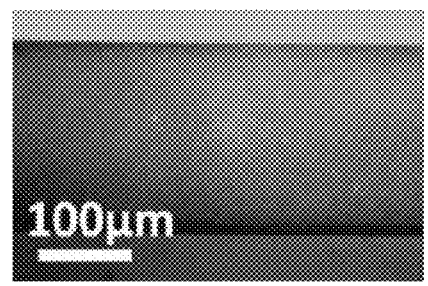
Figure 4G:
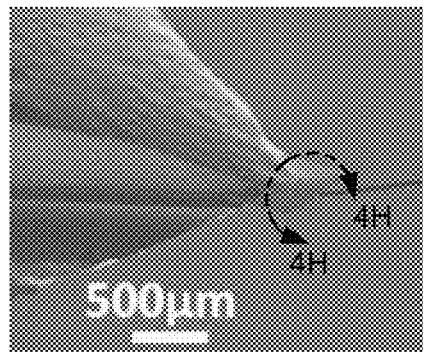
Figure 4H:
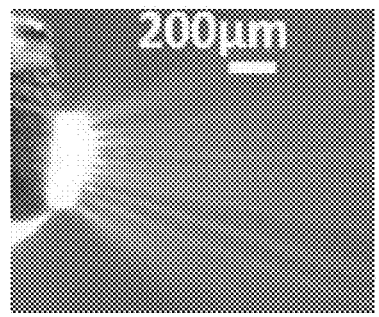

FIG. 4C shows an example of a schematic illustration of an iMS chip, with enlarged photographs of portions to the iMS chip including the cell trap (FIG. 4D), frits for channel packing with media (FIG. 4E), the media-packed processing channel (FIG. 4F), and the emitter (e.g., a multinozzle emitter) (FIGS. 4G and 4H). The multinozzle emitter shown in FIGS. 4G and 4H includes 10 nozzles, each with an inner diameter of about 10 microns, before and during electrospray. Other multinozzle emitter configurations are possible. The dimensions of the enrichment channel and the separation channel (width×depth×length) shown in FIG. 4C are about 1000 microns×100 microns×0.5 cm and about 200 microns×100 microns×4.5 cm, respectively. Dimensions for other components are specified with scale bars. Other dimensions of the enrichment and separation channels and other features of an iMS chip are possible.

In some embodiments, a plurality of iMS chip channels, associated sample input holes, and associated emitters may be included on an iMS chip. For example, the first wafer, the second wafer, and the transparent wafer may each be substantially circular, with the plurality of iMS chip channels being arranged about an axis of the first wafer, the second wafer, and the transparent wafer. Such an iMS chip including a plurality of iMS chip channels may be used with a system similar to the system described with respect to FIGS. 3A and 3B; the system for use of an iMS chip including a plurality of iMS chip channels may also include features for imaging, however.

Experiments Using an iMS Chip

Figure 5A:
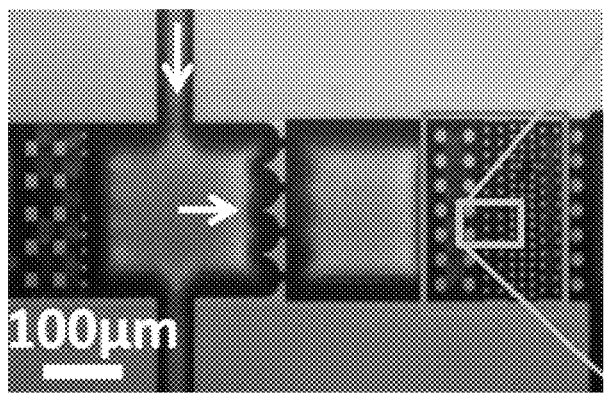
FIGS. 5A and 5B show examples of photographs of a series of micropillar arrays with varying inter-pillar sizes ranging from 10 microns to 2 microns configured to capture cells based on their sizes.
Figure 5B:
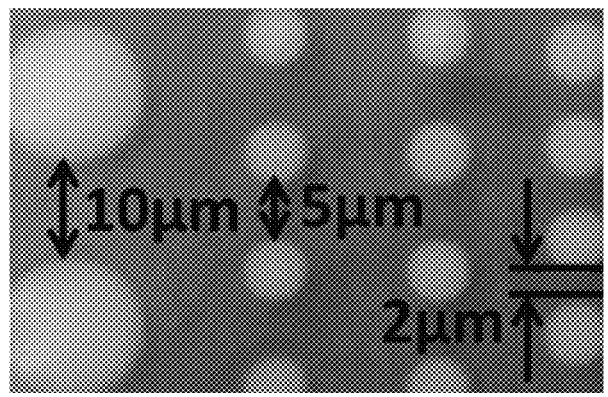

The following description of experiments using a iMS chip are intended to be examples of the embodiments disclosed herein, and are not intended to be limiting. The performance of each component of an iMS chip was tested individually, including the components for cell capture, single-cell imaging, cell lysis, on-chip liquid chromatography, and online nanoelectrospray mass spectrometry detection of tryptic peptides. For on-chip cell capture, imaging, and lysis, human breast cancer cell line MDA-MB-231 were used. Cells were cultured, harvested after trypsinization, stained with DAPI, and delivered into the cell trap using a syringe by the hydrodynamic flow with an active pressure control on the corresponding reservoirs. A series of micropillar arrays with varying inter-pillar sizes ranging from 10 microns to 2 microns were implemented to capture cells based on their sizes, as shown in FIGS. 5A and 5B. MDA-MB-231 cells were trapped in both 10 micron and 5 micron filter regions, but not 2 micron filter regions, consistent with the known size heterogeneity among cancer cells. Since the iMS chip can provide single-cell capture in real time, one could envision its potential applications in enumerating cancer cells, for example, circulating tumor cells, with fluorescence microscopy. It was further shown that the iMS chip is suitable for processing the captured cells for downstream biochemical analysis (e.g., MS) of cellular components. Captured MDA-MB-231 cells were completely lysed after on-chip lysis with detergents. More complex components for size- and/or affinity-based cell separation may be incorporated into the cell trap for capturing cells of interest with high specificity and sensitivity. For direct downstream LC-MS/MS applications, different methods for cell lysis including detergent treatment, laser-induced lysis, mechanical disruption, high electrical fields, and freezing/thawing may be used.

Method of Fabrication of an iMS Chip

FIGS. 6A-6J show examples of cross-sectional schematic illustrations an iMS chip during different stages in a fabrication process for the iMS chip. The fabrication operations for iMS chips are consistent with conventional microfabrication processes and can be adapted to mass production. The procedures for microfabrication of the iMS chip may include ten operations, as shown in FIGS. 6A-6J, and similar to what has been described for $M^3$ emitters (see, e.g., U.S. Pat. No. 8,022,361) and a MEA chip (see, e.g., International Application No. PCT/US12/45082).

Figure 6A:
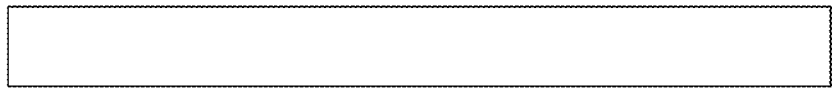
FIGS. 6A-6J show examples of cross-sectional schematic illustrations of an iMS chip during different stages in a fabrication process for the iMS chip.
Figure 6B:
Figure 6C:
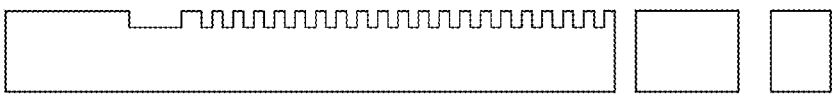
Figure 6D:
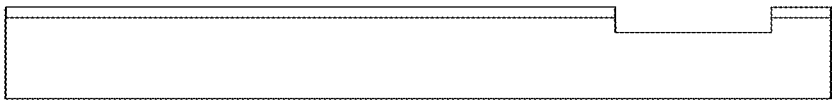
Figure 6E:
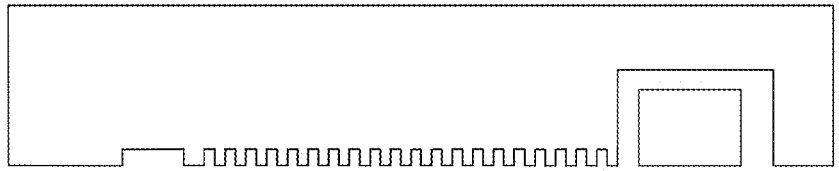
Figure 6F:
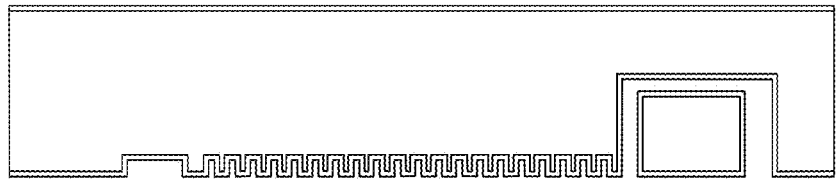
Figure 6G:
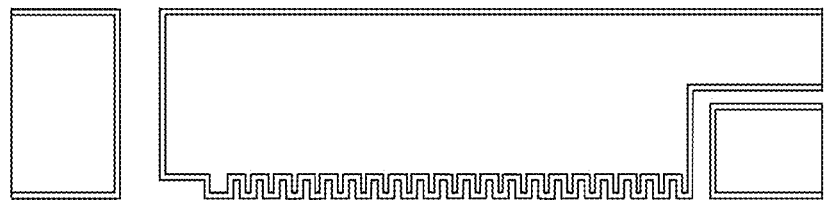
Figure 6H:
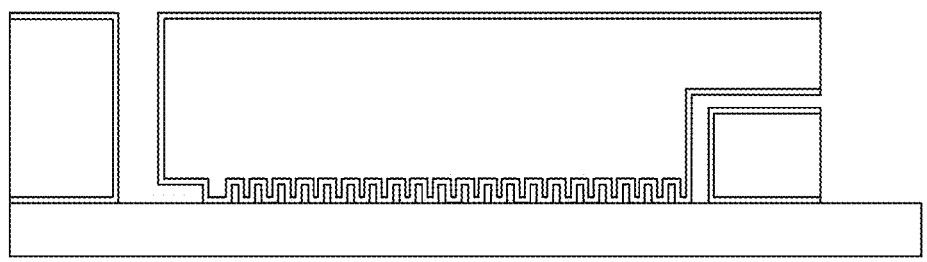
Figure 6I:
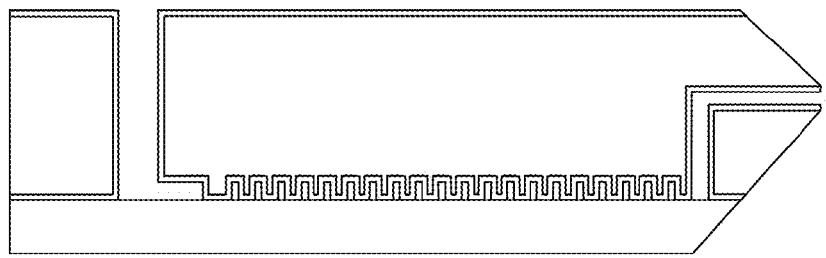
Figure 6J:
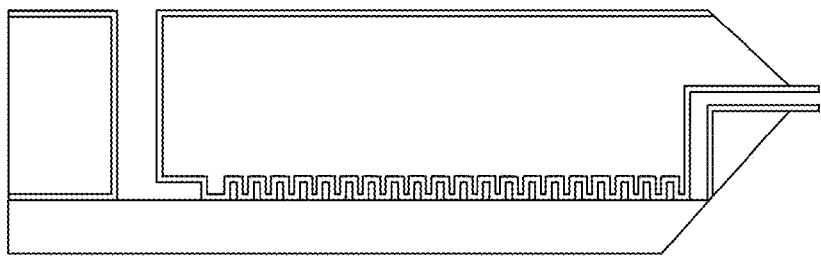

First, the wafers are cleaned with a piranha solution. In some embodiments, the wafers may include silicon wafers (e.g., 6-inch silicon wafers) (FIG. 6A). The use of silicon wafers or wafers of another semiconductor material may allow the features of the iMS chip to be more easily fabricated. Then, photolithography is performed to pattern a proteome processor (i.e., the cell trap, frits, and channels) on one silicon wafer, and the wafer is etched to produce trenches with a specified depth by deep reactive ion etching (DRIE) (FIG. 6B). Then, another photolithography and DRIE through-wafer etching operation is performed to create access holes or reservoirs for fluidic connection between the layers and oxidant species during thermal oxidation (FIG. 6C). Next, a photolithography and DRIE operation is performed to create emitters on another silicon wafer (FIG. 6D). Then, the wafer pair is cleaned, aligned, and brought into contact to form a spontaneous bond. Annealing in a furnace at about 1050° C. for about 1 hour, with nitrogen ($N_2$) flow, is used to create a covalent (e.g., silicon-silicon) fusion bond (FIG. 6E). Next, an oxide is formed on all silicon surfaces, including the sealed channels/emitters (FIG. 6F). In some embodiments, the oxide may be about 0.5 microns to 1.5 microns thick, or about 1 micron thick. In some embodiments, the oxide may be formed with a thermal oxidation process or a wet thermal oxidation process. Afterwards, another photolithography and through-wafer etching (e.g., DRIE) operation is performed to create access holes for sample injection/outside tubing connection and to sharpen the left and right sides of the emitters (FIG. 6G). Then, anodic bonding of the silicon wafer pair with a glass wafer is performed (FIG. 6H). After dicing the bonded wafer, the top and bottom sides of emitters are polished and sharpened on individual chips (e.g., with sand paper) (FIG. 6I). Finally, the nozzles were protruded by selective xenon difluoride ($XeF_2$) silicon etching (FIG. 6J).

Summary

In summary, in some embodiments, a silicon-based, scalable, and integrated MEA chip has the potential to become an enabling platform for MS-based small-volume proteomics. On-chip and on-line LC-MS analysis of microliters of human blood was demonstrated. On MEA chips, multinozzle emitters improve MS sensitivity, and on-chip and on-line multichannel LCs increase throughput. Detection of full-length proteins and their tryptic peptides on a unified platform facilitates protein identification, characterization, and quantitation. A 24-plex MEA chip also opens up the possibility of multiplex analysis of multi-class analytes in parallel from a single sample on the same platform. For example, by packing separate LC channels using C4 and C18 beads, the plasma proteome at both protein and peptide levels can be characterized. $TiO_2$ beads for on-chip enrichment of phosphopeptides and phosphoproteins for phosphoproteomics can also be used. The throughput of MEA chips can be further increased by integrating more channels (e.g., from 24 to 96) and by optimizing the LC operation to increase the MS duty cycle using a strategy of staggered parallel separations. If incorporated with cell processing and on-chip protein digestion, plus automatic fluidic switching among on-chip LCs, and further interfaced with quantitative proteomics strategies such as multiple reaction monitoring (MRM) and "sequential window acquisition of all theoretical fragment-ion spectra" (SWATH), the MEA chip can serve as a low-cost, fully-integrated, high-sensitivity, and high-throughput platform for multiplexed proteomics of small-volume biospecimens.

Further, in some embodiments, a silicon-based iMS chip may bridge a gap in the monolithic coupling between advanced bioimaging and nanoelectrospray mass spectrometry on a silicon-based microfluidic chip. On-chip single cell capture, imaging, and lysis, LC separation, and MS identification has been demonstrated using such an iMS chip. The iMS chip may be incorporated in a fully integrated and high-throughput platform, for example, to include components for cell culture and stimulation, and to implement massively-parallel iMS chips (e.g., 96 units on a 6-inch wafer). This may enable real-time monitoring, processing, and biochemical characterization of a small number of cells down to single cells. This may further provide new opportunities for biological and pathological studies of stem cells and cancer through single cell omics.

The subject matter disclosed herein is also described in the publication Pan Mao, Rafael Gomez-Sjoberg, and Daojing Wang, "Multinozzle Emitter Array Chips for Small-Volume Proteomics," Anal Chem. 2013 Jan. 15; 85(2):816-9, and in the manuscript by Pan Mao, Hung-Ta Wang, Peidong Yang, and Daojing Wang, "iMS-Chip: Integrating Imaging and Mass Spectrometry on a Silicon-based Microfluidic Chip," both of which are herein incorporated by reference.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:
1. An apparatus comprising:
a first wafer;
a second wafer, the first and second wafers comprising silicon wafers and defining a sample input hole, the second wafer defining a first portion of a first channel, the first channel including a first end and a second end, the first end of the first channel proximate to and fluidly coupled to the sample input hole, the first channel configured to contain separation media;
an emitter, the emitter being disposed between the first wafer and the second wafer, the second end of the first channel proximate to and fluidly coupled to the emitter; and
a transparent wafer being an optically transparent glass wafer configured to define a second portion of the first channel, the transparent wafer being bonded to a bottom surface of the second wafer, wherein the bond is an anodic silicon-glass bond, and wherein the first wafer, the second wafer, and the transparent wafer are monolithically integrated,
the transparent wafer being further configured to be transparent along the second portion of the first channel to provide an imaging window of an entirety of the separation media included in the first channel, wherein the second wafer is disposed between the first wafer and the transparent wafer.

2. The apparatus of claim 1, wherein the second end of the first channel includes a frit configured to retain separation media in the first channel.

3. The apparatus of claim 1, further comprising:
separation media disposed in the first channel, wherein the separation media includes a coating configured for separation of the sample into specific molecules.

4. The apparatus of claim 1, further comprising:
separation media disposed in the first channel, wherein the separation media includes beads, and wherein the beads are substantially spherical and have a diameter of about 1 micron to 50 microns.

5. The apparatus of claim 1, further comprising:
one or more channels, in addition to the first channel, forming a plurality of channels.

6. The apparatus of claim 5, wherein the first wafer and the second wafer are each substantially circular, and wherein the plurality of channels are arranged about an axis of the first wafer and the second wafer.

7. The apparatus of claim 5, wherein the one or more channels have a plurality of channel dimensions that are the same as the first channel.

8. The apparatus of claim 1, wherein the first channel has a cross-section of about 100 microns to 300 microns by about 100 microns to 300 microns.

9. The apparatus of claim 1, wherein the first channel has a length of about 3 centimeters to 15 centimeters.

10. The apparatus of claim 1, wherein the first wafer and the second wafer include through vias configured to allow fastening hardware to pass through the first wafer and the second wafer.

11. The apparatus of claim 1, wherein the sample input hole has dimensions of about 500 microns to 1.5 millimeters.

12. The apparatus of claim 1, wherein the sample input hole is a through via in the first wafer.

13. An apparatus comprising:
an emitter;
a first wafer;
a second wafer, the first and second wafers comprising silicon wafers, the first wafer and the second wafer defining a sample input hole, the first wafer and the second wafer defining a first exit channel having a first end and a second end, the emitter being disposed between the first wafer and the second wafer, the second end of the first exit channel proximate to and fluidly coupled to the emitter; and
a transparent wafer being an optically transparent glass wafer, the second wafer and the transparent wafer defining a first channel having a first end and a second end, the first end of the first channel proximate to and fluidly coupled to the sample input hole, the second end of the first channel proximate to and fluidly coupled to the first end of the first exit channel, the first channel being configured to contain separation media,
wherein the transparent wafer is bonded to a bottom surface of the second wafer, wherein the bond is an anodic silicon-glass bond, wherein the first wafer, the second wafer, and the transparent wafer are monolithically integrated, wherein the transparent wafer is configured to be transparent along the first channel to provide an imaging window of an entirety of the separation media included in the first channel, and wherein the second wafer is disposed between the first wafer and the transparent wafer.

14. The apparatus of claim 13, further comprising:
one or more channels and exit channels, in addition to the first channel and the first exit channel, forming a plurality of channels and exit channels.

15. The apparatus of claim 14, wherein the first wafer, the second wafer, and the transparent wafer are each substantially circular, and wherein the plurality of channels and exit channels are arranged about an axis of the first wafer, the second wafer, and the transparent wafer.

16. The apparatus of claim 14, wherein the one or more additional channels and exit channels have a plurality of dimensions that are the same as the first channel and the first exit channel.

* * * * *